(12) United States Patent
Westwick et al.

(10) Patent No.: US 8,498,695 B2
(45) Date of Patent: Jul. 30, 2013

(54) IMAGING SYSTEM WITH A SINGLE COLOR IMAGE SENSOR FOR SIMULTANEOUS FLUORESCENCE AND COLOR VIDEO ENDOSCOPY

(75) Inventors: Paul Westwick, Vancouver (CA); David Potkins, White Rock (CA); John Fengler, North Vancouver (CA)

(73) Assignee: Novadaq Technologies Inc., Mississauga (CA)

( * ) Notice: Subject to any disclaimer, the term of this patent is extended or adjusted under 35 U.S.C. 154(b) by 1177 days.

(21) Appl. No.: 11/964,330

(22) Filed: Dec. 26, 2007

(65) Prior Publication Data

US 2008/0239070 A1    Oct. 2, 2008

Related U.S. Application Data (60) Provisional application No. 60/908,373, filed on Mar. 27, 2007, provisional application No. 60/876,597, filed on Dec. 22, 2006.

(51) Int. Cl.
*A61B 6/00* (2006.01)

(52) U.S. Cl.
USPC ............ 600/478; 600/109; 600/160; 600/178

(58) Field of Classification Search
USPC  348/65, 68, E5.029, E7.085, E9.01; 600/109, 600/160, 178, 473, 476, 478
See application file for complete search history.

(56) References Cited

U.S. PATENT DOCUMENTS

| | | | | |
|---|---|---|---|---|
| 5,208,651 | A * | 5/1993 | Buican | 356/451 |
| 5,840,017 | A * | 11/1998 | Furusawa et al. | 600/160 |
| 6,293,911 | B1 | 9/2001 | Imaizumi et al. | |
| 6,315,712 | B1 * | 11/2001 | Rovegno | 600/109 |
| 6,462,770 | B1 * | 10/2002 | Cline et al. | 348/65 |
| 6,510,338 | B1 * | 1/2003 | Irion et al. | 600/476 |
| 6,652,452 | B1 * | 11/2003 | Seifert et al. | 600/140 |
| 6,821,245 | B2 * | 11/2004 | Cline et al. | 600/160 |
| 6,899,675 | B2 * | 5/2005 | Cline et al. | 600/160 |
| 7,179,222 | B2 | 2/2007 | Imaizumi et al. | |
| 7,420,151 | B2 * | 9/2008 | Fengler et al. | 250/208.1 |
| 7,479,990 | B2 | 1/2009 | Imaizumi et al. | |
| 7,697,975 | B2 * | 4/2010 | Zeng | 600/473 |
| 7,811,229 | B2 * | 10/2010 | Sugimoto | 600/160 |
| 8,140,147 | B2 * | 3/2012 | Maynard et al. | 600/476 |
| 2001/0028458 | A1 * | 10/2001 | Xiao | 356/417 |
| 2002/0155619 | A1 * | 10/2002 | Kurihara et al. | 436/172 |
| 2002/0161282 | A1 * | 10/2002 | Fulghum | 600/160 |
| 2003/0117491 | A1 * | 6/2003 | Avni et al. | 348/77 |
| 2003/0191368 | A1 * | 10/2003 | Wang et al. | 600/160 |
| 2005/0288593 | A1 * | 12/2005 | Georgakoudi et al. | 600/476 |

(Continued)

OTHER PUBLICATIONS

US 6,692,429, 02/2004, Imaizumi et al. (withdrawn)

*Primary Examiner* — Lashonda Jacobs (74) *Attorney, Agent, or Firm* — Novak Druce Connolly Bove + Quigg LLP (57) ABSTRACT

An endoscopic video system and method using a camera with a single color image sensor, for example a CCD color image sensor, for fluorescence and color imaging and for simultaneously displaying the images acquired in these imaging modes at video rates in real time is disclosed. The tissue under investigation is illuminated continuously with fluorescence excitation light and is further illuminated periodically using visible light outside of the fluorescence excitation wavelength range. The illumination sources may be conventional lamps using filters and shutters, or may include light-emitting diodes mounted at the distal tip of the endoscope.

18 Claims, 9 Drawing Sheets

U.S. PATENT DOCUMENTS

| | | | |
|---|---|---|---|
| 2006/0004292 A1* | 1/2006 | Beylin | 600/476 |
| 2009/0114799 A1 | 5/2009 | Maeda | |
| 2009/0114803 A1 | 5/2009 | Yamaguchi | |
| 2009/0122135 A1 | 5/2009 | Matsui | |
| 2009/0122152 A1 | 5/2009 | Yamaguchi et al. | |
| 2009/0124854 A1 | 5/2009 | Yamaguchi et al. | |
| 2009/0290149 A1* | 11/2009 | Roth | 356/300 |
| 2010/0110168 A1* | 5/2010 | Avni et al. | 348/68 |

* cited by examiner

First field readout values

| A1 | G+Cy | Mg+Ye | G+Cy | Mg+Ye |
| A2 | Mg+Cy | G+Ye | Mg+Cy | G+Ye |

Second field readout values

| B1 | G+Cy | Mg+Ye | G+Cy | Mg+Ye |
| B2 | Mg+Cy | G+Ye | Mg+Cy | G+Ye |

First field readout values

| A1 | Cy | Ye | Cy | Ye |
| A2 | Cy | Ye | Cy | Ye |

Second field readout values

| B1 | G | Mg | G | Mg |
| B2 | Mg | G | Mg | G |

Timing Diagram Details

| Time | Full CCD illumination for interval from $T_i$ to $T_{i+1}$ | CCD Lines | CCD signal read out | Signal ID | Display signal written to buffer | Color image | Fluorescent image |
|---|---|---|---|---|---|---|---|
| T1 | Fluorescence + Full color | Even | Fluorescence only | F1 | (FL6 = F6 + F1) | | (FL6) |
| T2 | Fluorescence only | Odd | Fluorescence + Full color | C1 | (CL12 = C12 + C1) | (CL12 – FL6) | |
| T3 | Fluorescence only | Even | Fluorescence + Full color | C2 | CL1 = C1 + C2 | (CL1 – FL6) | |
| T4 | Fluorescence + Full color | Odd | Fluorescence only | F2 | FL1 = F1 + F2 | | FL1 |
| T5 | Fluorescence only | Even | Fluorescence + Full color | C3 | CL2 = C1 + C3 | CL2 – FL1 | |
| T6 | Fluorescence only | Odd | Fluorescence + Full color | C4 | CL3 = C3 + C4 | CL3 – FL1 | |
| T7 | Fluorescence + Full color | Even | Fluorescence only | F3 | FL2 = F2 + F3 | | FL2 |
| T8 | Fluorescence only | Odd | Fluorescence + Full color | C5 | CL4 = C3 + C5 | CL4 – FL2 | |
| T9 | Fluorescence only | Even | Fluorescence + Full color | C6 | CL5 = C5 + C6 | CL5 – FL2 | |
| T10 | Fluorescence + Full color | Odd | Fluorescence only | F4 | FL3 = F3 + F4 | | FL3 |
| T11 | Fluorescence only | Even | Fluorescence + Full color | C7 | CL6 = C5 + C7 | CL6 – FL3 | |
| T12 | Fluorescence only | Odd | Fluorescence + Full color | C8 | CL7 = C7 + C8 | CL7 – FL3 | |
| T13 | Fluorescence + Full color | Even | Fluorescence only | F5 | FL4 = F4 + F5 | | FL4 |
| T14 | Fluorescence only | Odd | Fluorescence + Full color | C9 | CL8 = C7 + C9 | CL8 – FL4 | |
| T15 | Fluorescence only | Even | Fluorescence + Full color | C10 | CL9 = C9 + C10 | CL9 – FL4 | |
| T16 | Fluorescence + Full color | Odd | Fluorescence only | F6 | FL5 = F5 + F6 | | FL5 |
| T17 | Fluorescence only | Even | Fluorescence + Full color | C11 | CL10 = C9 + C11 | CL10 – FL5 | |
| T18 | Fluorescence only | Odd | Fluorescence + Full color | C12 | CL11 = C11 + C12 | CL11 – FL5 | |
| T1 | Fluorescence + Full color | Even | Fluorescence only | F1 | FL6 = F6 + F1 | | FL6 |
| T2 | Fluorescence only | Odd | Fluorescence + Full color | C1 | CL12 = C12 + C1 | CL12 – FL6 | |
| T3 | Fluorescence only | Even | Fluorescence + Full color | C2 | CL1 = C1 + C2 | CL1 – FL6 | |

IMAGING SYSTEM WITH A SINGLE COLOR IMAGE SENSOR FOR SIMULTANEOUS FLUORESCENCE AND COLOR VIDEO ENDOSCOPY

RELATED APPLICATIONS

This application claims the benefit of U.S. Provisional Application Ser. Nos. 60/876,597, filed Dec. 22, 2006, and 60/908,373, filed Mar. 27, 2007, the disclosures of all of which are incorporated herein by reference in their entirety as if fully set forth herein.

BACKGROUND OF THE INVENTION

The invention is directed to methods and systems for simultaneous real-time fluorescence and color video endoscopy at close to video frame rates. The invention is also directed to high-efficiency illumination sources and to methods and systems for controlling temporal and spectral output of these light sources.

Medical endoscopy is increasingly employing specialized optical imaging techniques, such as fluorescence (i.e. autofluorescence and photodynamic) endoscopy, narrow band imaging and other techniques, for improved visualization and for the detection and diagnosis of diseases. Endoscopic imaging systems that provide specialized imaging modes typically also operate in a conventional color, or white-light, endoscopy mode. Embodiments of endoscopic imaging systems incorporating both a color and fluorescence imaging modes have been disclosed, for example, in U.S. Pat. No. 6,462,770 B1, U.S. Pat. No. 6,821,245 B1, and U.S. Pat. No. 6,899,675 B2.

In conventional white-light endoscopy, hereinafter also referred to as color imaging mode, light in the visible spectral range is used to illuminate the tissue surface under observation. Light reflected by the tissue passes through a suitable lens system and is incident on an image sensor built into or attached to the endoscope. The electrical signals from the image sensor are processed into a full color video image which can be displayed on a video monitor or stored in a memory. In fluorescence endoscopy, fluorescence excitation light excites fluorophors in the tissue, which emit fluorescence light at an emission wavelength which is typically greater than the excitation wavelength. Fluorescence light from the tissue passes through a suitable lens system and is incident on the image sensor. The electrical signals from the image sensor are processed into a fluorescence video image which can be displayed on a video monitor, either separately from or together with the color video image, or stored in a memory.

The fluorescence excitation and emission wavelengths depend upon the type of fluorophors being excited. In the case of exogenously applied fluorophors, the band of excitation wavelengths may be located anywhere in the range from the ultraviolet (UV) to the near infra-red (NIR) and the emission wavelength band anywhere from the visible to the NIR. For fluorophors endogenous to tissue, the band of excitation and emission wavelengths are more limited (excitation from the UV to the green part of the visible spectrum, emission from the blue-green to the NIR).

In a conventional fluorescence/white-light endoscopic imaging system, the system can be switched between color and fluorescence modes either automatically or with a hand- or foot-operated external switch. Both the illumination and imaging characteristics of the endoscopic imaging system may require adjustment when switching the operation of an endoscopic imaging system from one mode to the other. For example, gain adjustments and additional image processing (e.g., pixel binning, time averaging, etc.) may be required because the image signal in color imaging mode tends to be substantially greater than the image signal from endogenous (tissue) fluorescence. Although switching between imaging modes with an automated device is not difficult, additional time may be required to complete the endoscopic procedure because areas of interest are examined sequentially in each mode.

It would therefore be desirable to provide an endoscopic imaging system capable of acquiring and displaying images in both conventional color ("white-light") and fluorescence imaging modes simultaneously. It would further be desirable to employ high-efficiency illumination sources that can be easily controlled over the spectral range of interest for endoscopy.

SUMMARY OF THE INVENTION

The invention disclosed herein describes an endoscopic video system and method using a single color image sensor for fluorescence and color imaging and for simultaneously displaying the images acquired in these imaging modes at video rates. The color imager may include a CCD color image sensor. The endoscopic video system has no moving parts.

According to one aspect of the invention, tissue is illuminated continuously with fluorescence excitation light and is further illuminated periodically using visible light outside of the fluorescence excitation wavelength range. The method furthermore utilizes an excitation light blocking filter which substantially blocks the excitation light while allowing the blue, green and red components of the illumination light to pass to the color image sensor. In one embodiment, the single color image sensor may be disposed in the tip of the endoscope, in which case the excitation light blocking filter is mounted in or on the tip of video endoscope.

With the method of the invention, fluorescence images are acquired during a time period when only the excitation light is supplied as illumination, while color images are acquired during a time period when the combination of both excitation light and visible light outside of the excitation wavelength range are supplied as illumination. The image fields are read out from the single CCD color image sensor in an interlaced fashion and processed to produce corresponding full-frame fluorescence and white-light images. Real-time fluorescence and white-light images of the tissue are then produced by subtracting from each full-frame combined fluorescence and white-light image the corresponding fluorescence image on a pixel-by pixel basis.

In one embodiment, the illumination light may be switched on for one cycle and switched off for two cycles, wherein a different image field of the combined tissue fluorescence and white-light image is read out during each of the two cycles when the illumination light is switched off, and a different image field of the tissue fluorescence image are read out during each of the cycles when the illumination light is switched on. A cycle may have a duration of 1/60 second. Four full frame white-light images and two full frame fluorescence images may be generated every six cycles.

The image data can be interpolated during cycles when no actual image data are available. For example, during a cycle where no full frame white-light image is produced, an interpolated full frame white-light image may be computed from two adjacent full frame white-light images. Likewise, the fluorescence signals may be interpolated between sequential fluorescence frames before being subtracted from the white-light image signals.

In yet another embodiment, pixel values of adjacent rows of the CCD color image sensor are added pixel-by-pixel to form summed row pixel values and the summed values are read out in an interlaced fashion.

In one embodiment, a high-resolution video image may be generated by computing a luma image of the combined full-frame fluorescence and white-light image signals and colorizing the luma image based on a ratio of red reflectance to fluorescence signals to produce a superimposed fluorescence/color image for display. Processing an image based on the luma data enhanced the attainable spatial resolution. A change in tissue pathology, as indicated by a change in the fluorescence signal from that tissue, can be represented as a change in color in the video image.

Further features and advantages of the present invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIG. 8 shows a timing diagram for reading from the color sensor fluorescence and color image information;

DETAILED DESCRIPTION

In conventional white-light (color imaging) endoscopy, broadband visible light is used to illuminate the tissue under observation. Historically, endoscopes used for white light endoscopy have incorporated fiberoptic light guides to transmit light from lamps to provide this type of illumination. In fluorescence endoscopy, fluorophors in the tissue are excited by illumination with a shorter wavelength light and the resulting fluorescence emission is detected at Stokes-shifted longer wavelengths. The fluorophors may be either endogenous to the tissue (i.e., naturally present) or exogenous (e.g., dyes applied to enhance contrast for diagnostic or other imaging purposes). Since the fluorescence process tends to be rather inefficient, the intensity of the shorter wavelength excitation light is typically several orders of magnitude greater than the intensity of the resulting fluorescence emission. As such, both direct visualization and imaging of emissions from fluorophors requires the use of a barrier filter that blocks transmission of the reflected shorter wavelength excitation light and prevents the excitation light from overwhelming the eye or image sensor used to observe/detect the emitted fluorescence. A certain minimum level of excitation light intensity is also required to provide the desired quality of (optical or electronic) image signal. The desired amount of excitation light will depend on the type and concentration of fluorophors to be excited, distance to the tissue and size of the area being visualized imaged, the sensitivity of the eye/image sensor and similar related factors. As a result, particularly in the case of natural (i.e., endogenous) tissue fluorescence, endoscopy imaging systems operating in fluorescence mode typically employ powerful arc lamps or lasers to excite fluorophors as well as highly sensitive cameras to image fluorescence emissions from these fluorophors.

Figure 1:
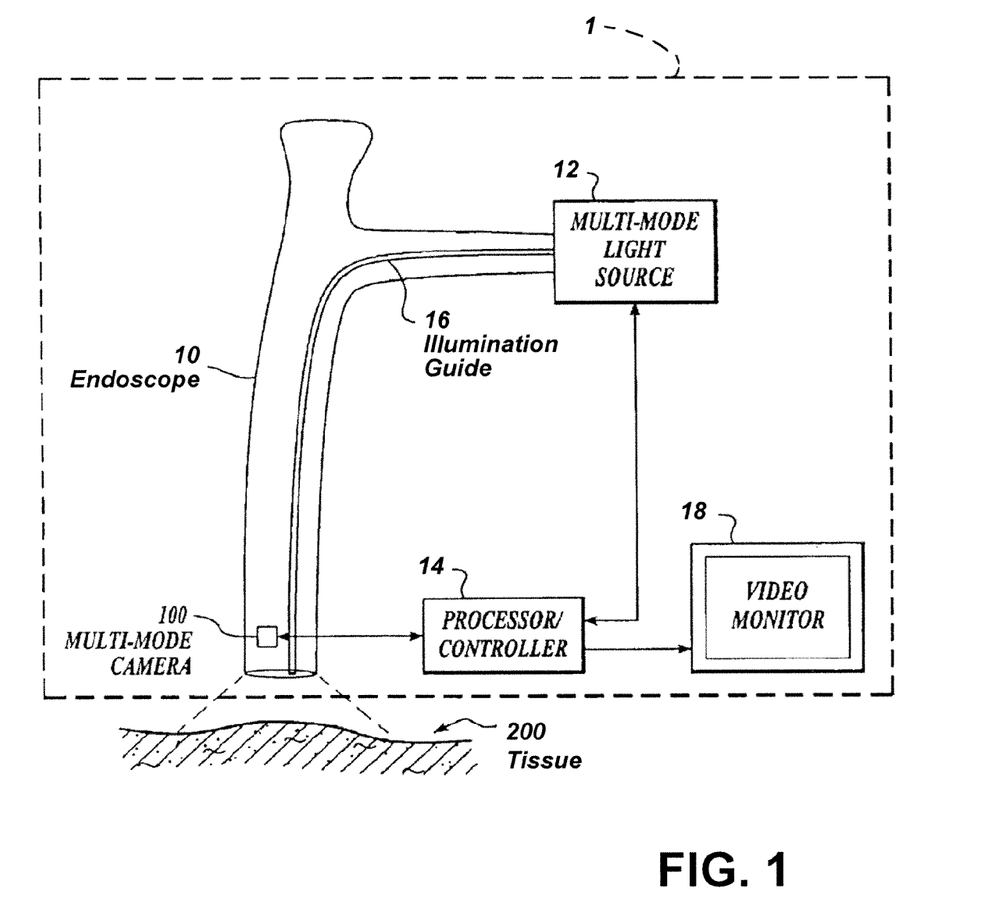
FIG. 1 shows a schematic block diagram of an exemplary fluorescence endoscopy video system with a single distal color image sensor.

FIG. 1 is a block diagram of a fluorescence endoscopy video system 1 in accordance with one embodiment of the present invention. The system includes a multi-mode light source 12 that generates light for obtaining color and fluorescence images. The use of the light source for obtaining different kinds of images will be described in further detail below. Light from the light source 12 is supplied to an illumination guide 16 of an endoscope 10, which then illuminates a tissue sample 200 that is to be imaged.

As also shown in FIG. 1, the system also includes a camera 100, for example, a solid-state camera based on a CCD or CMOS sensor chip, which in the exemplary embodiment is located at the distal or insertion end of the endoscope 60. Alternatively, although not illustrated, the camera 100 may also be positioned at another location, such as the proximal end of the endoscope 60. In the depicted embodiment, the light from the tissue is directly captured by the camera 100, and the operation of the system is similar to video endoscopes currently on the market (such as the Olympus CF-240L).

A processor/controller 14 controls the camera 100 and the light source 12, which will be described in more detail below, and produces video signals that are displayed on a video monitor 18. The processor/controller 14 communicates with the camera 100 by wire or other signal communication devices that are routed within the endoscope, such as optical fiber. Alternatively, communication between the processor/controller 14 and the camera 100 can be conducted over a wireless link. Clinically relevant information about the health of the tissue under observation may be contained in the intensity of the fluorescence emission within a specific wavelength range.

For autofluorescence endoscopy (endoscopy using endogenous fluorophors), such information is contained in the green wavelength range of the emitted fluorescence. It has been observed that green florescence is increasingly suppressed as the tissue becomes increasingly diseased. However, the red fluorescence signal does not vary with the disease state of the tissue and can hence be used to distinguish between intensity variation in the green fluorescence emission due to the disease state of the tissue and intensity variations due to imaging artifacts, such as shadows or geometry effects (e.g., imaging distance). A single multicolor image can be formed in which the color is indicative of the health of the examined tissue by combining the image information from a wavelength range that varies with the disease state (green fluorescence) with the image information from a wavelength range that does not vary with the disease state (red fluorescence) of the tissue.

Figure 2:
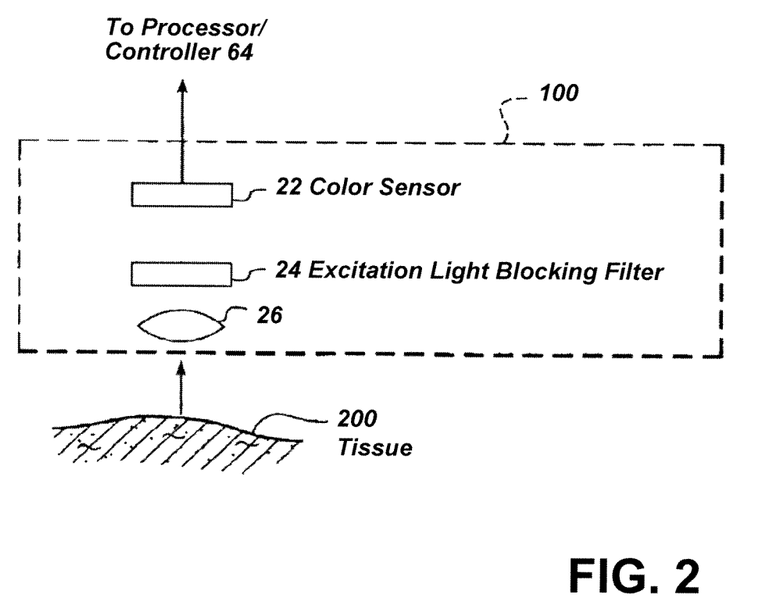
FIG. 2 shows the camera of FIG. 1 with an excitation light blocking filter.

FIG. 2 shows schematically an exemplary embodiment of camera 100 with color image sensor 22 and light collimating optics 26. Positioned between the tissue 200 and color image sensor 22 is an excitation light blocking filter 24 which blocks reflected excitation light from reaching image sensor 22, while allowing imaging light and fluorescence light to pass. The advantage of this configuration is that all imaging is performed and controlled by the same imaging optics 113. In an alternative embodiment, the excitation light blocking filter 24 may be placed distal of the light collimating optics 26, and in some embodiments may be disposed on the outside of the distal tip of the endoscope, for example, when converting a white-light imaging endoscope into an imaging/fluorescence endoscope. An externally mounted excitation light blocking filter is described in, for example, commonly assigned U.S. application Ser. No. 11/412,715.

The white light/fluorescence video endoscopy system of the invention operates by illuminating the sample with either excitation light alone or with a combination of excitation light and illumination light in a wavelength range or in wavelength ranges outside the spectral range of the excitation spectrum. The light source for excitation light and illumination light can be, for example, an arc lamp, a solid state light emitter such as one or more diode lasers or light emitting diodes, or any other light source emitting light in a suitable wavelength range. The light source can be a single light source, wherein a portion of the light is filtered out to provide excitation light, and another portion of the light is filtered out to provide illumination light. Alternatively, different light sources can be provided for excitation light and illumination light, respectively. The illumination light is timed, either by using an external shutter 37 or, if light sources with a rapid response are used, by turning the light sources on and off.

Figure 3:
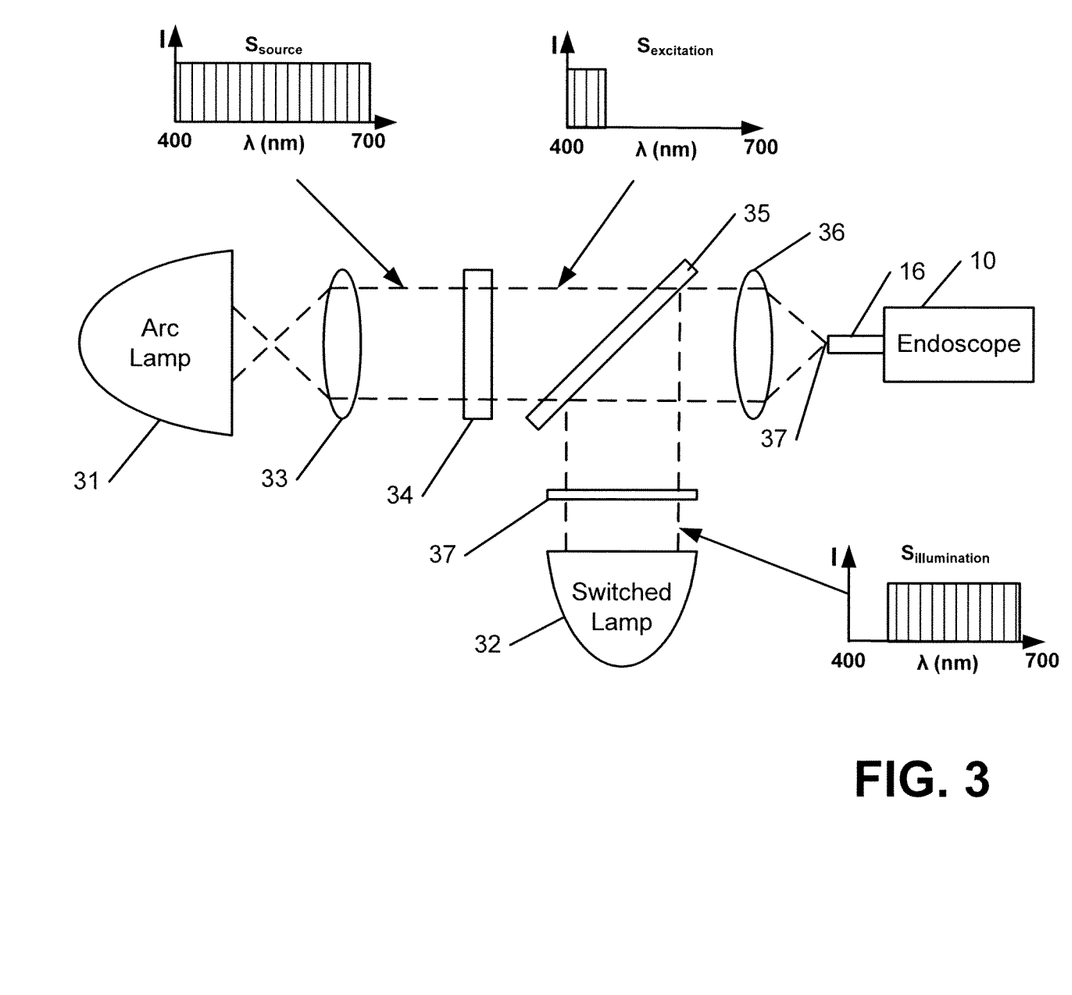
FIG. 3 shows a schematic block diagram of a first exemplary embodiment of an illumination source according to the invention.

FIG. 3 shows in more detail a first embodiment of a multi-mode light source 30 for simultaneously illuminating a tissue sample 200 with continuous fluorescence excitation light and switched illumination light. Light source 30 includes a first light source 31, for example, an arc lamp, and a collimating lens 33 for producing a high intensity, preferably collimated spectral output $S_{source}$ which includes an excitation wavelength range. A bandpass filter 34 filters out spectral components outside the excitation wavelength range $S_{excitation}$ and allows only spectral components within the excitation wavelength range $S_{excitation}$ to pass. Light source 30 further includes a second light source 32, for example, a halogen lamp, for producing a preferably collimated spectral output $S_{illumination}$ with a high intensity in an imaging wavelength range covering, for example, the visible spectral range. Light source 32 may be switched with timing signals produced by processor/controller 14, for example, by placing a mechanical or electronic shutter 37 between second light source 32 and dichroic mirror 35 or by controlling the electric current supplied to light source 32. The combined collimated excitation/imaging light is focused by lens 36 onto the input face 37 of an optical fiber illumination guide 16 with a suitable numerical aperture (NA).

Figure 4:
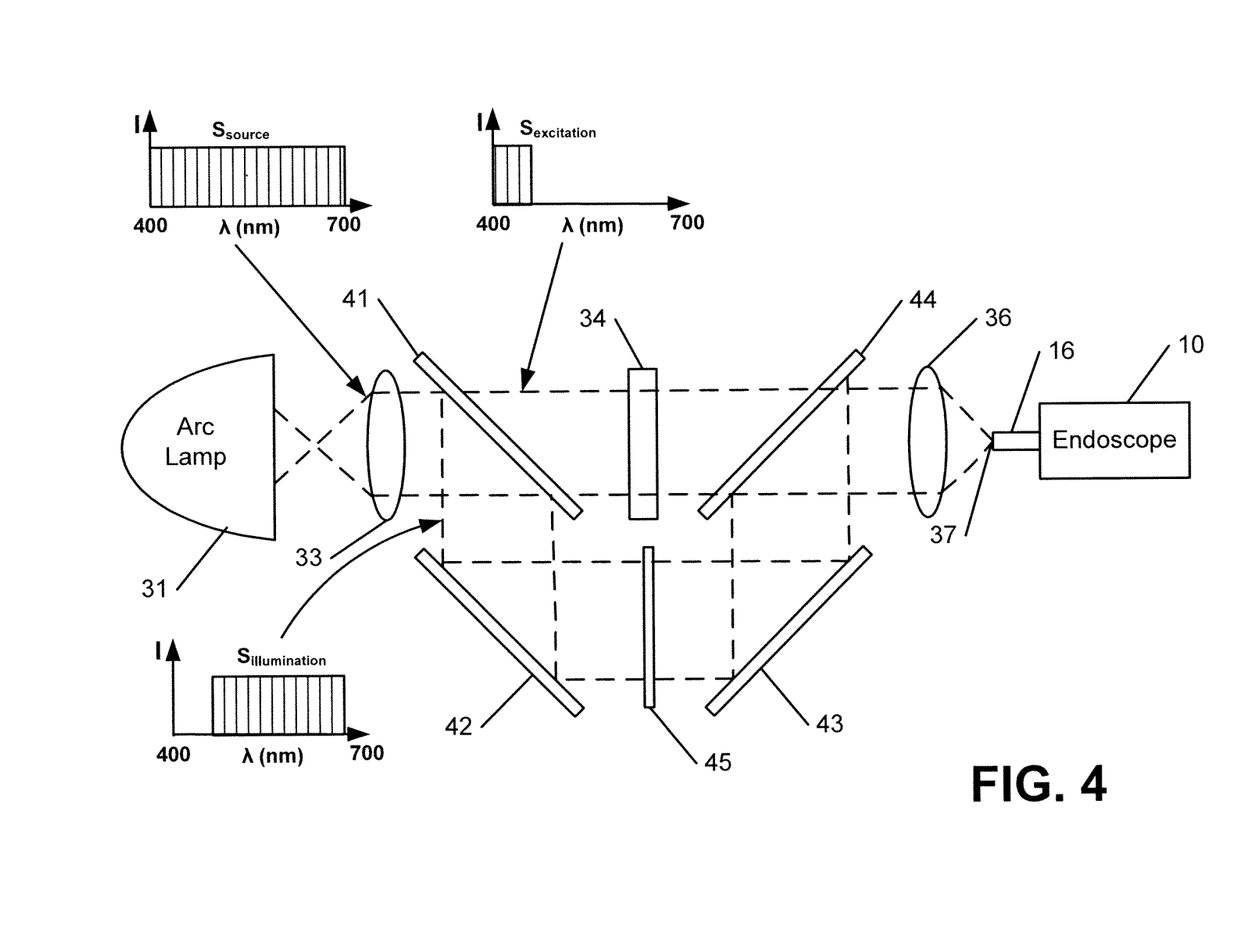
FIG. 4 shows a schematic block diagram of a second exemplary embodiment of an illumination source according to the invention.

FIG. 4 shows a second embodiment of a multi-mode light source 40 for simultaneously illuminating a tissue sample 200 with continuous fluorescence excitation light and switched illumination light. Light source 40 includes an excitation/illumination light source 31, for example, an arc lamp, and a collimating lens 33 for producing a high intensity, preferably collimated spectral output $S_{source}$ which includes an excitation wavelength range $S_{excitation}$. A dichroic mirror 41 reflects the spectral illumination component $S_{illumination}$ and passes the excitation wavelength range $S_{excitation}$ which may be additionally narrow-band filtered by bandpass filter 34. The light component reflected off a first dichroic mirror 41 is then reflected by mirror 42, passes through a shutter 45 (mechanical or electronic) and is then further reflected by mirror 43 and reflected at second dichroic mirror 44 to become collinear with the excitation light passing through filter 34. As before, the combined collimated excitation/imaging light is focused by lens 36 onto the input face 37 of an optical fiber illumination guide 16 with a suitable numerical aperture (NA). This embodiment takes advantage of the fact that a suitable arc lamp can emit over a wavelength range which covers both the excitation light spectrum and the illumination light spectrum. The shutter 45 may be switched by timing signals produced by processor/controller 14.

Suitable filters, for example, a low-pass filter to block excitation light and/or a high-pass filter to block unswitched illumination light, may be placed along the optical paths.

In operation, when the switched light source 32 is off (or the shutter 45 is closed), only excitation light illuminates the tissue 200, for example, through the endoscope illumination guide 16. The reflected excitation light is blocked from reaching the color image sensor by the excitation light blocking filter 24, while tissue fluorescence light passes through the excitation light blocking filter 24 and reaches the color image sensor 22 for fluorescence light detection.

When the illumination light source 32 is switched on (or the shutter 45 is open), the combined light from the illumination light source 32 and the excitation light source 31 is coupled into the endoscope light guide 14 and illuminates the tissue 200. The reflected excitation light (and any residual light from the switched light source at that wavelength) is blocked as before by the excitation light blocking filter 24, while the combination of both tissue fluorescence and reflected illumination light ("white light") is imaged by the color image sensor 22.

Figure 5A:
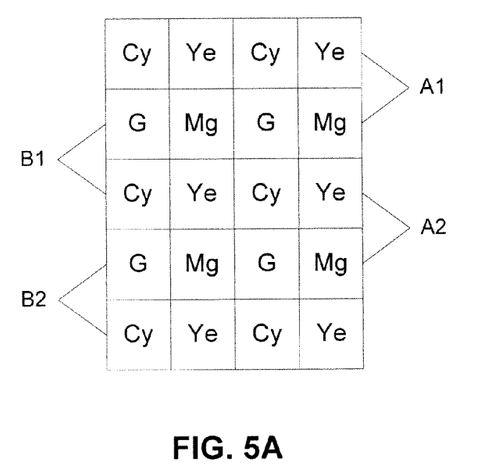
FIG. 5 shows a filter arrangement on a CMGY image sensor (A) and interlaced readout (B) with summing on chip.
Figure 5B:
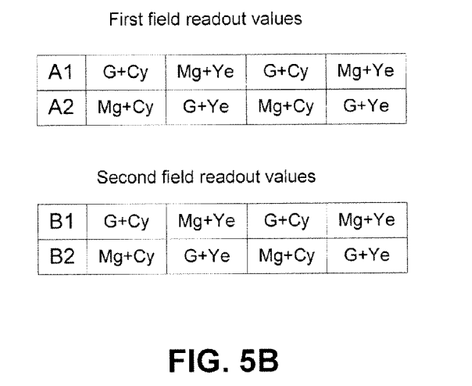
Figure 6A:
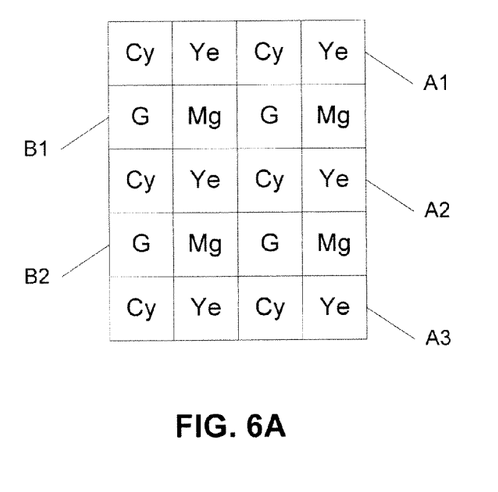
FIG. 6 shows a filter arrangement on a CMGY image sensor (A) and interlaced readout (B) without summing on chip.
Figure 6B:
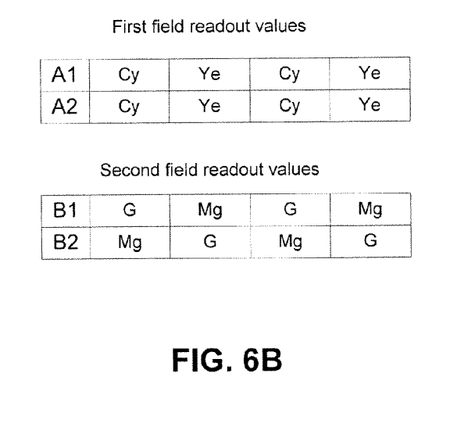

FIG. 5 shows an exemplary arrangement of spectral filter elements disposed on the pixels of a CMGY image sensor (FIG. 5A) and an interlaced readout (FIG. 5B) with on-chip summing of pixels from adjacent rows. The first half-frame in the embodiment depicted in FIGS. 5A, 5B is here composed of the sum of lines 1 and 2; 3 and 4; 5 and 6; and so on, whereas the second half-frame is composed of the sum of lines 2 and 3; 4 and 5; and so on. FIG. 6A shows the same filter arrangement as in FIG. 5A, but with a different interlaced readout (FIG. 5B) without on-chip summing. The first half-frame in the embodiment depicted in FIGS. 6A, 6B is composed of lines 1; 3; 5; and so on, whereas the second half-frame is composed of the lines 2; 4; and so on.

Most video endoscopes and endoscopic video cameras currently use CCD image sensors with CMGY color filters since these tend to provide the highest quality color images.

Figure 7:
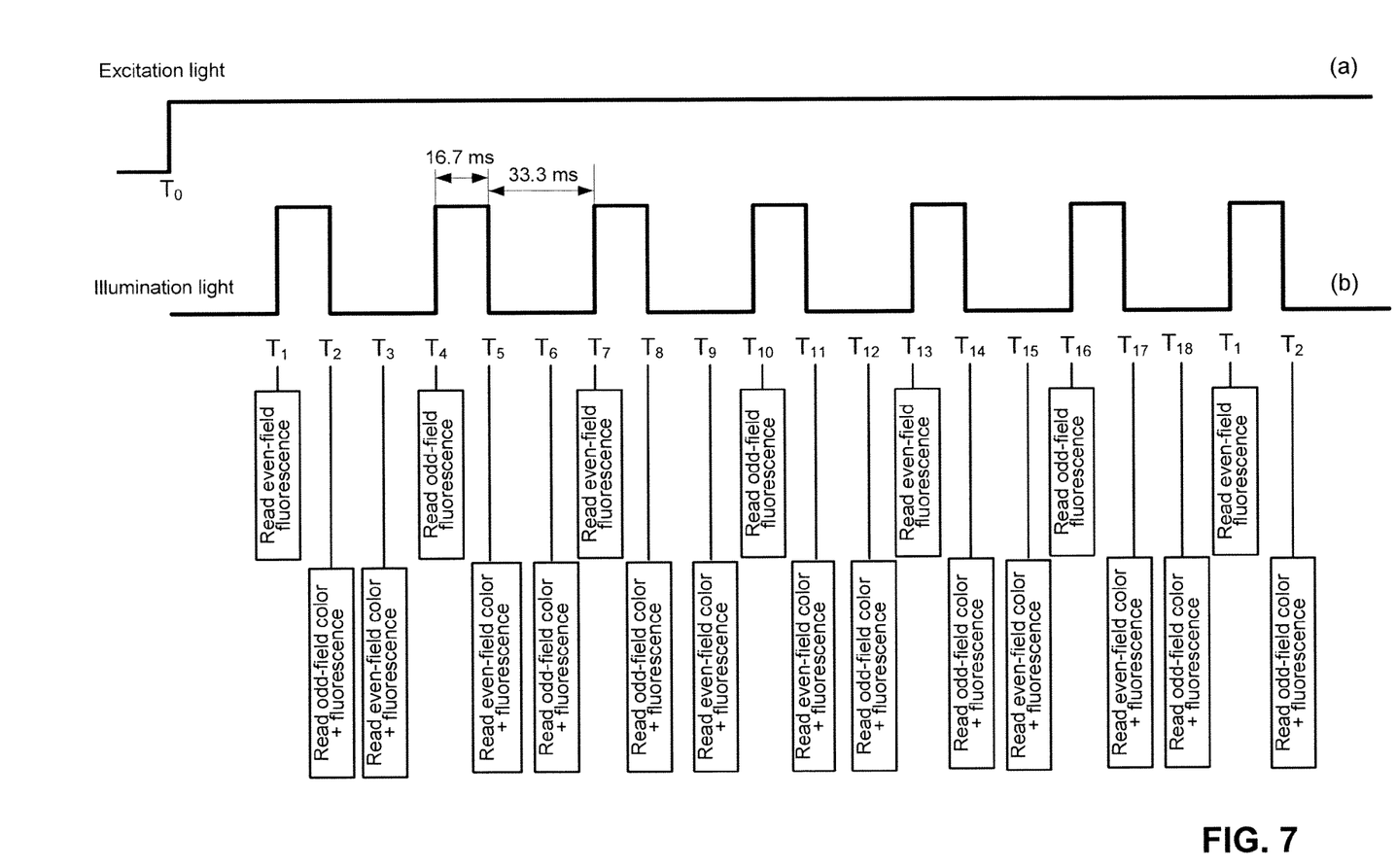
FIG. 7 shows a timing diagram for excitation light and imaging light exposure.

FIG. 7 shows a timing diagram according to the invention for operating the exemplary endoscope system. As can be seen from curve (a) in the diagram, the excitation light source 31 is turned on at time $T_0$, irradiating the tissue continuously with fluorescence excitation light. Conversely, as depicted by curve (b), the illumination light source 32 is periodically switched on and off (or shutter 37 or 45 is opened and closed) with a duty factor of 33%, i.e. the illumination light source is turned on at times $T_1, T_4, T_7, \ldots$ (i.e., at times $T_{1+3*n}$ with n=0, 1, 2, ...) for one field period and turned off again at times $T_2, T_5, T_8, \ldots, T_{2+3*n}$ for two field periods, which include times $T_3, T_6, T_9, \ldots, T_{3+3*n}$. In the depicted example, a field period has a duration of 1/60 s=16.7 ms.

As mentioned above, the exemplary image sensor is read out in an interlaced fashion, so that even lines and odd lines are read alternatingly, with or without summation on the chip. An image with full vertical resolution is then generated in the video processor/controller 14 by combining two sequential interlaced fields to form a full video frame for the fluorescence image and for the combined fluorescence/white-light image.

FIG. 8 describes in more detail the temporal illumination and readout pattern of the interlaced CCD image as a function of time.

Before the image acquisition begins in the depicted example at time $T_1$, the CCD is illuminated only with fluorescence excitation light. The even-fields acquired in the time interval preceding $T_1$ contain fluorescence-only data which are read out at $T_1$. At the same time, the illumination light is turned on, so that the CCD is now illuminated with fluorescence excitation light and illumination light between the times $T_1$ and $T_2$.

The illumination light is turned off at time $T_2$, in the present example after 16.7 ms, and the image data representing "color-plus-fluorescence" are read out for the odd field at $T_2$ and for the even field at $T_3$. The CCD is illuminated from $T_2$ until $T_4$ with fluorescence light only and acquires a new fluorescence signal. It should be noted that the fluorescence signal is acquired during two field periods, whereas the added illumination light is acquired only during one field period, which provides an improved signal over other methods, where the fluorescence signal and the illumination signal are acquired with the same duty cycle.

The image signals from the color image sensor acquired alternatingly during "fluorescence-only" and "color-plus-fluorescence" measurements are supplied to processor/controller 14 which stores and processes the image signals to form the desired images for display. The processor/controller 14 may be, for example, a processor selected from the Texas Instruments C64XX family of image processors. The processing of a specific field depends on whether the field is to be used to generate a fluorescence image or a color (white tight) image. The processor/controller 14 may also synchronize the operation of the switched illumination light source with the image acquisition, as described above.

This exposure and read-out scheme described above generates from the combination of odd and even fields a full frame of fluorescence image information every six field time periods. In the depicted example, each field time period is 16.7 ms. In other words, the full frame fluorescence image is completely updated every tenth of a second. During the same six (6) field periods, four fields (two even fields and two odd fields) of color image information are generated and these even- and odd-line fields are suitably combined and processed to generate four (4) full vertical resolution color video frames during the same six (6) field periods. As seen in column 6 of FIG. 8, the display signal written into buffer memory still includes the fluorescence signal component, which is then subtracted to yield the color image signal. The transformation of image data from the CMGY image space to the RGB image space for display is conventional and will not be described further.

Because during six (6) field periods the image data contain only 2 (two) fields of color information, rather than three (3) video frames, the image data may advantageously be interpolated between sequential data points. In this way, the image quality can be improved by providing a smooth transition between frames, so that the final color video image is perceived by the human eye as being substantially similar to the field update rate in a normal video signal.

Once the image signals in Column 6 of FIG. 8 are transferred to the image processor 14, the color (white-light) images and the fluorescence images are separated on a frame-by-frame basis. The color information is extracted from these frames (i.e. the contribution from the fluorescence signal is removed) by subtracting pixel-by-pixel a fluorescence signal value from each "color-plus-fluorescence" frame. Advantageously, the subtracted fluorescence signal values are interpolated from the preceding stored "fluorescence-only" frame and the "fluorescence-only" frame following the "color-plus-fluorescence" frame being processed. This causes at most a delay of two fields, in the present example of 66.7 ms, between image acquisition and display.

After the fluorescence contribution is subtracted, the color balance of the remaining image signals may still need to be corrected for proper white balance. This correction may be performed using conventional image processing and color-space transformation methods by using a compensation matrix or similar processing techniques, which convert the image signal from one color space to another. The processing of fluorescence image fields is somewhat less complex because the fluorescence image data do not include image data from other sources. Accordingly, fluorescence image data produced in multiple, non-overlapping spectral ranges may be processed and displayed as a real color or false color image (for example, green fluorescence from fluorescein) may be displayed as green and IR fluorescence from ICG may be displayed as red, etc., in the same fashion as white light color images are processed and displayed on a video monitor. Using this type of fluorescence imaging display for autofluorescence or endogenous tissue fluorescence imaging, areas of tissue in which the green fluorescence is suppressed due to abnormal pathology will appear red since the red fluorescence is proportionally less suppressed.

The processor/controller circuit 14 can carry out inter-image computation for superimposing a fluorescence image and a white-light light image on video monitor 18. An operator can therefore view the fluorescence image and the white-light light image simultaneously, without introducing a perceptible time delay between them. Consequently, for example, the location of a lesion can be readily viewed with high precision, which is very useful for diagnosis.

Figure 9:
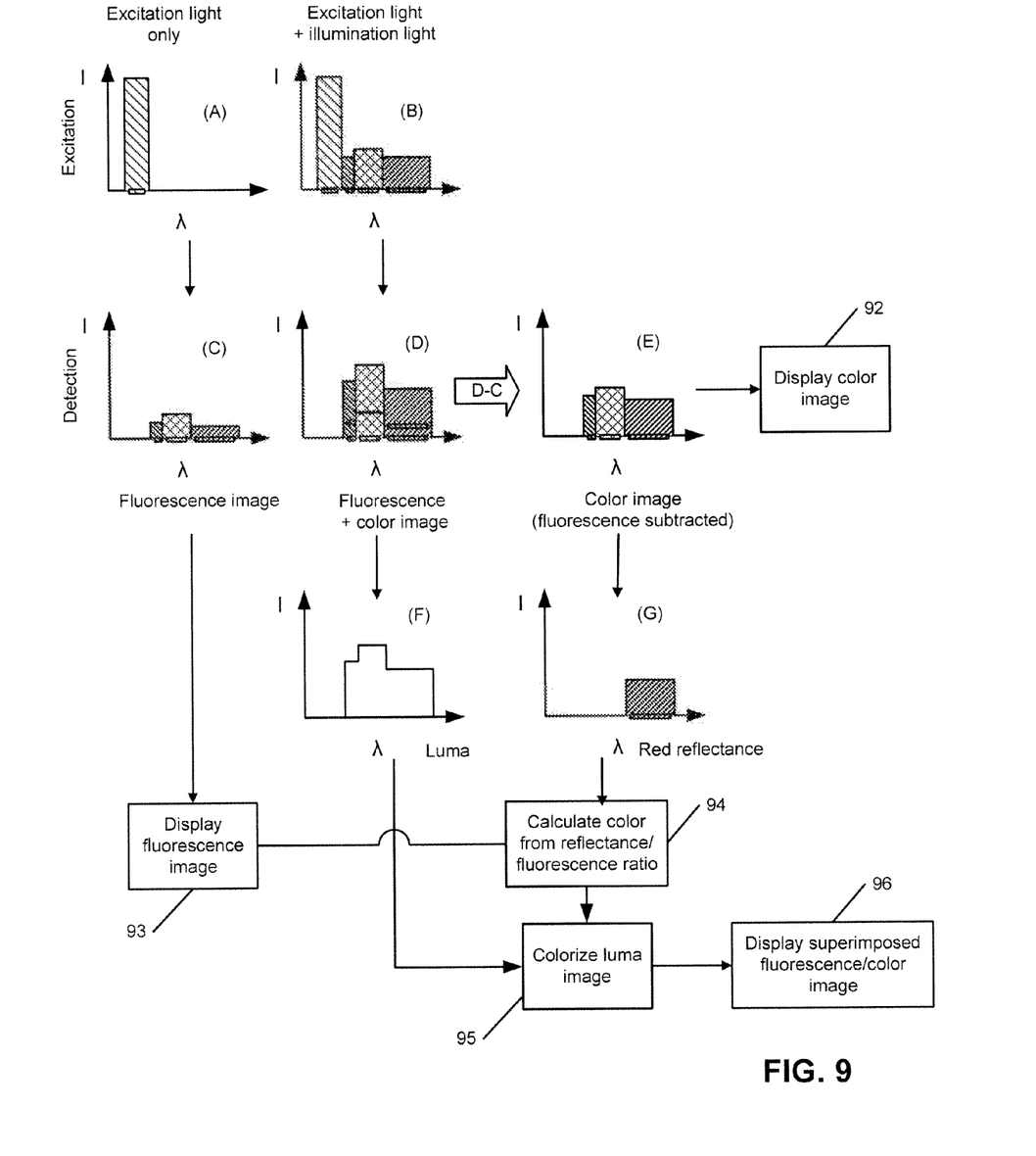
FIG. 9 shows schematically block diagram of a process according to the invention for extracting fluorescence and color images.

FIG. 9 illustrates schematically a process flow which may be performed, for example, by processor/controller 14, to extract fluorescence images and reflectance images, and to correct image intensity and color information for improving spatial resolution and for simultaneously displaying fluorescence/reflectance images.

The depicted process assumes that the excitation light, labeled (A) in FIG. 9, is emitted in the blue/UV spectral range, for example, for exciting fluorescence in fluorescein, which is detected in the green spectral range. However, other fluorescent dyes such as ICG which has excitation/fluorescence wavelengths in the red/IR spectral range can also be used, and the present invention is not limited to particular fluorescent materials or wavelengths. Illumination light is emitted at wavelengths outside the excitation light wavelengths and is shown together with the excitation light in FIG. 9 as (B).

When the tissue is illuminated with fluorescence light only, e.g., during the time interval between $T_0$ and $T_1$ (FIG. 7), a fluorescence spectrum (C) is detected by color sensor 22. When the tissue is illuminated with fluorescence light+illumination light, e.g., in the time interval between $T_1$ and $T_2$ (FIG. 7), a fluorescence+color image spectrum (D) is detected by color sensor 22. The fluorescence spectrum (C) is then subtracted from the fluorescence+color image spectrum (D) to produce the spectral response of the color image (E). This color image can then be displayed at 92.

Advantageously, the "luma" component of the fluorescence+color image is extracted, shown as (F). Luma refers to the brightness in an image, i.e., the not-gamma-corrected "black and white" or achromatic portion of the image. Stated differently, luma represents the achromatic image without any color, while the chroma components represent the color information. The luma component can be used for extracting more accurate spatial information from the image data.

In one embodiment, the red reflectance signal (G) is extracted from the color image frames. A ratio of fluorescence to red reflectance for spatially corresponding pixels in the fluorescence and color video frames is calculated, at 94, on a pixel-by-pixel basis, and the value of that ratio is used to determine the color (chroma) of the display pixel at that same location, at 94. The color of a display pixel is assigned such that ratio values that indicate suppressed green fluorescence and abnormal pathology are rendered in a contrasting color to pixels in which the ratio values are characteristic of normal green fluorescence values indicating normal tissue pathology. Although the color (chroma) of the display pixels is based upon a ratio of fluorescence to reflectance signal for that pixel, the brightness (luma) of each display pixel may simply be taken as the brightness (luma) of each color video frame pixel. Because the color, or white-light, video fields are updated at near video rates (i.e. 4 times in a 6 field period, see FIGS. 7 and 8), the resulting fluorescence/reflectance image brightness defining the luma will also be updated at that rate. Conversely, the chroma portion of the fluorescence/reflectance image will be updated somewhat more gradually (due to the less frequent field update rate of the fluorescence image signals). However, the human eye is less sensitive to changes in color than to changes in brightness, so that the slower fluorescence field update rate will be less objectionable in the image display and can still be regarded as a real-time image. The luma image (F) can then be colored according to the chroma information derived from the red reflectance (G).

Normalizing a fluorescence image by a red light image is advantageous, because the color of mucosa inside a human body is dominated by hemoglobin which is a pigment and predominantly absorbs light with wavelengths shorter than 600 nm. The reference image used for normalization should therefore represent reflected wavelengths of 600 nm or longer. The normalized fluorescence image can then be used as an accurate representation of the intensity of actual fluorescence or the degree of accumulation of an antibody labeled, for example, by indocyanine green (ICG). Normalization of a fluorescence image is not limited to normalization relative to a red light image. Alternatively, an image depicted by infrared fluorescence components may be used for the normalization.

It should be mentioned that for removing excitation light, the excitation light blocking filter 24 in FIG. 2 may be replaced by a dichroic mirror which reflects the spectral components of the excitation light.

Recent developments in solid state lighting technology have given rise to the use of solid state devices, such as light-emitting diodes (LEDs) and lasers, as sources of endoscopic illumination which may eventually replace the lamps 31 and 32 in the multimode light source 12. Since LEDs are very compact, inexpensive, reliable, and have a long lifetime (on the order of 10,000 hours or longer, depending on the drive current), incorporation of this illumination technique in endoscopic medical equipment will lead to lower cost endoscopic light sources and hence also to less expensive endoscopes.

Solid state illumination sources, in particular LEDs, with emission wavelengths ranging from the deep UV to the infrared spectral range, have recently become available. These LEDs have several advantages which makes them particularly suitable for endoscopy: they can be manufactured to have a narrow, controllable spectral emission range which may be tuned to the fluorescence excitation spectra of the fluorophors; they are very efficiently in converting electric input power to optical output power; they can be rapidly switched on and off; and their power output can be adjusted by varying the electric current through the device which facilitates control and timing of the spectral output of an LED-based illumination source.

Figure 10A:
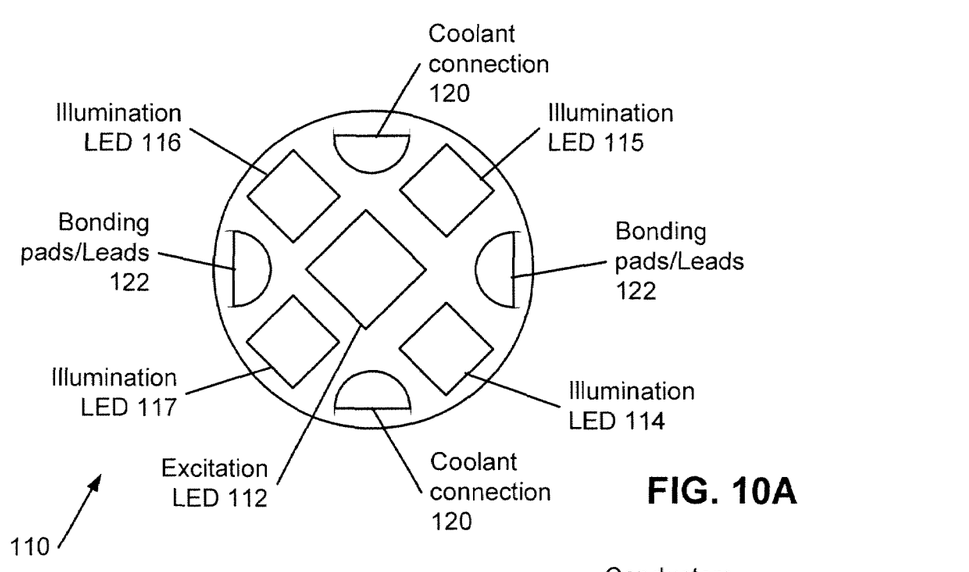
FIGS. 10A and 10B illustrate an LED assembly configured as a multi-wavelength illumination source for endoscopy.
Figure 10B:
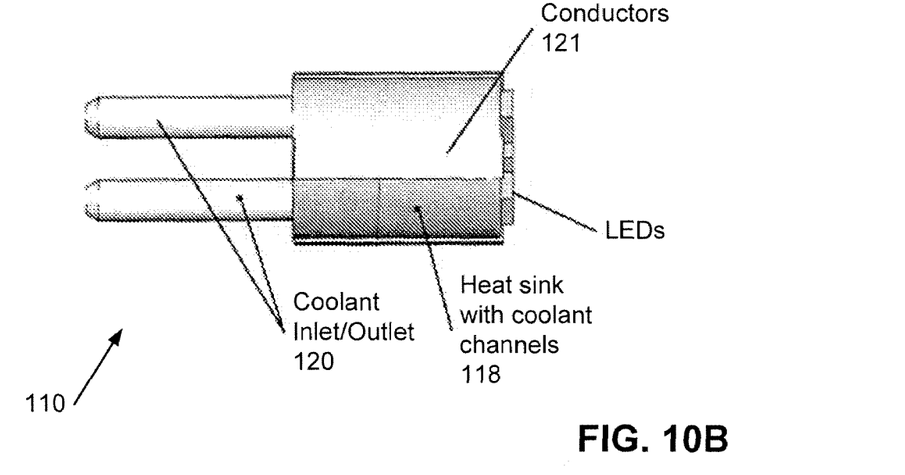

Due to their small die size, LEDs may be disposed at or incorporated in the distal tip of an endoscope. For example, as shown schematically in FIGS. 10A and 10B, several LEDs mounted on a common carrier can provide both narrow-band shorter wavelength excitation light for fluorescence endoscopy and broader visible illumination light for white-light endoscopy. FIG. 10A is a schematic top view of an illumination assembly 110 with an excitation, e.g. UV LED 112 die for providing excitation light, which is surrounded by blue (CWL 470 nm), green (CWL 525 nm), (CWL 590 nm) amber and red (CWL 630 nm) LED dies 114, 115, 116, 117 that provide illumination light. The indicated wavelengths are exemplary only and not intended to limit the scope of the invention. Also indicated are bonding pads 122 to electrically connect the LEDs to external wires (not shown). In general, more than the two indicated bonding pads may be provided. Each of the LEDs may be controlled individually.

In another embodiment not shown in the drawings, a so-called "white" LED which generates illumination light covering the visible spectral range can be employed instead of separate blue, green, red, and amber LEDs. "White" LEDs convert blue or UV radiation emitted by the blue- or UV-emitting LED die to visible light by downconversion of the blue- or UV-emission with a suitable phosphor. Both types of LEDs have recently become commercially available. Advantageously, the LEDs can be lensed for efficient directional illumination of the target tissue. The excitation LED may emit light in any spectral range suitable for exciting fluorescence in a dye, such as in the blue for fluorescein and in the near IR for ICG.

It will be understood that light emitted by the illumination LEDs should not contain spectral components in a wavelength range where dye fluorescence is excited. To eliminate emission at excitation light wavelengths from reaching the tissue under examination, suitable cutoff or passband, for example notch filters, may be placed in the optical path of the separate color LEDs or the "white-light" LEDs of illumination assembly 110.

Although LEDs convert electric energy to optical energy very efficiently, they still generate a substantial amount of heat which may cause discomfort for the patient. These LEDs may therefore have to be cooled. As shown more clearly in FIG. 10B, the LEDs may be mounted on a heat sink 118 with a coolant inlet/outlet which can be connected to an external chiller. In general, devices for cooling the LEDs may include thermoelectric coolers, liquid-cooled heat exchangers, expansion coolers, microchannel coolers, thermo-siphon heat pipes, and the like.

The excitation light blocking filter 24 for the excitation light placed in front of the sensor may be designed to prevent transmission of blue or UV light produced by the white-light LED. Alternatively or in addition, the LED itself may be covered with a filter absorbing the blue or UV light from the LED dies.

A temperature sensor may be incorporated into the heat sink 118, or mounted in close vicinity to the LED array, for the purposes of
1. monitoring and adjusting the heat sink temperature, and
2. providing a safety mechanism by which a signal can be generated to reduce or interrupt the electrical power to the LEDs in the event of a failure in the heat sink cooling system.

While the invention has been disclosed in connection with the preferred embodiments shown and described in detail, various modifications and improvements thereon will become readily apparent to those skilled in the art. For example, although not illustrated in the drawings, the illumination sources, such as the arc lamp or halogen lamp, may be replaced with LEDs or lasers. Accordingly, the spirit and scope of the present invention is to be limited only by the following claims.

What is claimed is:

1. A method for real-time acquisition of fluorescence and white-light endoscopic images with a single CCD color image sensor, comprising the steps of:
   continuously illuminating tissue with fluorescence excitation light,
   during the continuous illuminating with fluorescence excitation light, periodically illuminating the tissue with illumination light covering the entire visible spectral range,
   detecting with the single CCD color image sensor tissue fluorescence from the tissue induced by the fluorescence excitation light when the tissue is not illuminated with the illumination light,
   detecting with the single CCD color imager a combined, simultaneous tissue fluorescence and white-light image from the tissue when the tissue is additionally illuminated with the illumination light,
   reading image fields from the single CCD color image sensor in an interlaced fashion,
   processing the image fields to produce corresponding full-frame fluorescence and white-light images,
   subtracting from each full-frame combined fluorescence and white-light image the corresponding fluorescence image on a pixel-by pixel basis, and
   displaying or storing the real-time fluorescence and white-light images of the tissue.

2. The method of claim 1, wherein the illumination light is switched on for one cycle and switched off for two cycles.

3. The method of claim 2, wherein a different image field of the combined tissue fluorescence and white-light image is read out during each of the two cycles when the illumination light is switched off.

4. The method of claim 2, wherein a different image field of the tissue fluorescence image are read out during each of the cycles when the illumination light is switched on.

5. The method of claim 1, further comprising summing pixel values of adjacent rows of the CCD color image sensor pixel-by-pixel to form summed row pixel values and reading the summed values in an interlaced fashion.

6. The method of claim 1, further comprising computing a luma image of the combined full-frame fluorescence and white-light image signals and colorize the luma image based on a ratio of red reflectance to fluorescence signals to produce a superimposed fluorescence/color image for display.

7. The method of claim 2, wherein a cycle has a duration of 1/60 second.

8. The method of claim 2, wherein four full frame white-light images are produced every six cycles.

9. The method of claim 8, wherein during a cycle where no full frame white-light image is produced, an interpolated full frame white-light image is computed from two adjacent full frame white-light images.

10. The method of claim 2, wherein two full frame fluorescence images are produced every six cycles.

11. The method of claim 1, wherein in the subtracting step, the fluorescence signals are interpolated between sequential fluorescence frames before being subtracted from the white-light image signals.

12. An endoscope system used for observing living tissue inside a body cavity, comprising:
   a single CCD color image sensor configured to receive an optical image and to output image signals;
   an illuminating device having a white light source that emits white light covering the entire visible spectral range, and an excitation light source that emits excitation light having a predetermined wavelength for exciting autofluorescence in the living tissue;
   a display device;
   a control system configured to control the illuminating device to illuminate the living tissue continuously with excitation light and additionally illuminate the living tissue periodically with the white light during the continuous illumination with the excitation light, and to control an image processing system to obtain from the image signals interlaced image fields of alternating fluorescence image signals and combined, simultaneous fluorescence and white-light image signals,
   the control system further configured to process the interlaced image fields to produce corresponding full-frame fluorescence and white-light light images, and to subtract from each full-frame of the combined fluorescence and normal light image the corresponding fluorescence image on a pixel-by pixel basis to generate a white-light image frame for display on the display device.

13. The endoscope system of claim 12, wherein the image processing system is configured to convert the combined fluorescence and white-light image signals into luma signals, and to process the luma signals into a full-frame colorable intensity image.

14. The endoscope system of claim 12, wherein the illuminating device comprises a solid state light source having separately controllable white-light and excitation light sources.

15. The endoscope system of claim 14, wherein the solid state light source comprises plurality of light-emitting diodes.

16. The endoscope system of claim 15, wherein the light-emitting diodes are disposed on a distal end of the endoscope system.

17. The endoscope system of claim 16, wherein the light-emitting diodes are externally cooled.

18. The endoscope system of claim 16, wherein the light-emitting diodes are externally cooled by way of thermoelectric coolers, liquid-cooled heat exchangers, expansion coolers, microchannel coolers, or thermo-siphon heat pipes, or a combination thereof.

* * * * *